United States Patent [19]

Van der Knaap

[11] Patent Number: Plant 6,239

[45] Date of Patent: Aug. 2, 1988

[54] CHRYSANTHEMUM PLANT NAMED SUNNY CASSA

[75] Inventor: Jacques C. M. Van der Knaap, De Lier, Netherlands

[73] Assignee: Fides, Handelskwekerij, De Lier, Netherlands

[21] Appl. No.: 821,534

[22] Filed: Jan. 22, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Sunny Cassa particularly characterized by its flat capitulum form and single daisy capitulum type; dark yellow ray floret color; diameter across the face of the capitulum of 35–55 mm, and yellow-green to yellow disc florets.

1 Drawing Sheet

1

The present invention comprises a new and distinct cultivar of Chrysanthemum, botanically known as *Dendranthema morifolium*, Ramat., previously *Chrysanthemum morifolium*, Ramat., and referred to by the cultivar name Sunny Cassa.

Sunny Cassa was originated from a spontaneous mutation of Cassa in a controlled breeding program in De Lier, The Netherlands in 1983. Sunny Cassa was discovered and selected as one flowering plant within a group of flowering plants of the cultivar Cassa by Jacques C. M. Van der Knaap in November of 1983 in a controlled environment in De Lier, The Netherlands.

The first act of asexual reproduction of Sunny Cassa was accomplished when vegetative cuttings were taken from the initial selection in February of 1984 in a controlled environment in De Lier, The Netherlands by a technician working under formulations established and supervised by Jacques C. M. Van der Knaap. Horticultural examination of selected units initiated in June of 1985 has demonstrated that the combination of characteristics as herein disclosed for Sunny Cassa are firmly fixed and are retained through successive generations of asexual reproduction.

Sunny Cassa has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Sunny Cassa which, in combination, distinguish this Chrysanthemum as a new and distinct cultivar:

1. Flat capitulum form.
2. Single daisy capitulum type.
3. Dark yellow ray floret.
4. Diameter across the face of the capitulum 35–55 mm.
5. Yellow-green (immature) to yellow (mature) disc florets.

Of the many commercial cultivars known to the present inventor, the most similar in comparison to Sunny Cassa is Cassa, disclosed in my pending U.S. plant patent application. In comparison to Cassa, Sunny Cassa has dark yellow ray floret color. The capitulum form and type and other characteristics of Sunny Cassa are similar to those same characteristics of Cassa.

2

The accompanying photographic drawing shows typical inflorescence and foliage characteristics of Sunny Cassa, the colors being as true as reasonably possible for color photographs of this type.

In the following description, color references are made to The Royal Horticultural Society Colour Chart. The color values were determined between 11:00 a.m. and 12:00 noon in April under natural day light at De Lier, The Netherlands.

Classification:

*Botanical.*—*Dendranthema morifolium*, Ramat., cv Sunny Cassa.

*Commercial.*—Cut daisy spray.

INFLORESCENCE

A. Capitulum:
- *Form.*—Flat.
- *Type.*—Single daisy.
- *Diameter across face.*—35–55 mm.

B. Corolla of ray florets:
- *Color (general tonality from a distance of three meters).*—Dark yellow.
- *Color (upper surface).*—RHS 9A.

C. Corolla of disc florets:
- *Color (mature).*—Yellow, approximately 7A.
- *Color (immature).*—141B-C, lightening upon maturity to predominantly 7A, with showing of yellow-green 141C in center.

D. Reproductive organs:
- *Androecium.*—Present in disc florets; numerous.
- *Gynoecium.*—Present in both disc and ray florets; numerous.

PLANT

A. General appearance:
- *Height.*—80 cm.

B. Foliage:
- *Color (upper surface).*—RHS 147B.
- *Color (under surface).*—RHS 147A.
- *Shape.*—Short lobed and finely serrated.

I claim:

1. A new and distinct Chrysanthemum plant named Sunny Cassa, as described and illustrated, and particularly characterized by its flat capitulum form and single daisy capitulum type; dark yellow ray floret color; diameter across the face of the capitulum of 35–55 mm, and yellow-green to yellow disc florets.

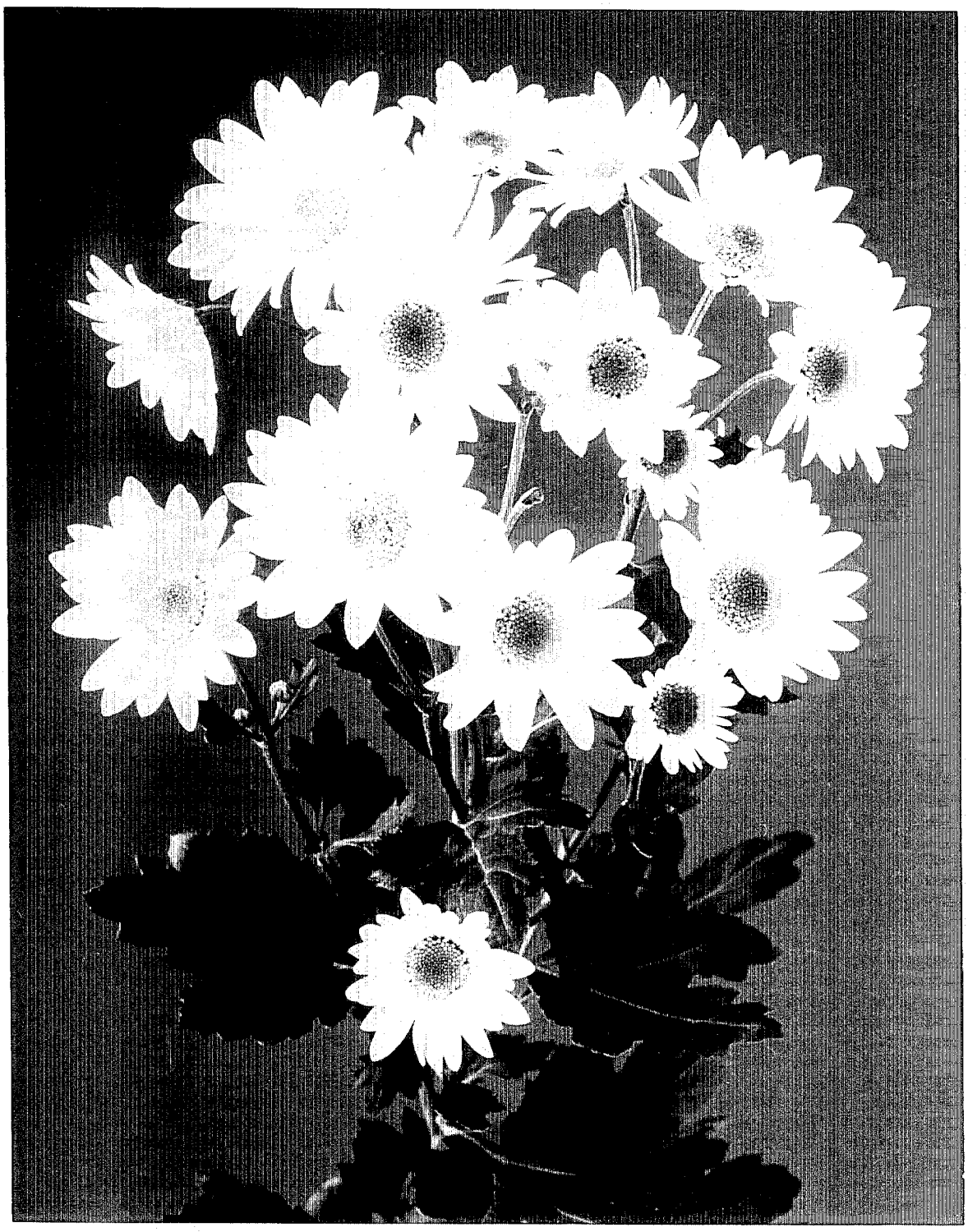

* * * * *